United States Patent
Ross et al.

(10) Patent No.: US 10,362,002 B2
(45) Date of Patent: Jul. 23, 2019

(54) METHODS AND SYSTEMS FOR JOURNALING AND COACHING USING A WEARABLE DEVICE

(71) Applicant: STRIIV, INC., Redwood City, CA (US)

(72) Inventors: Mark A. Ross, San Carlos, CA (US); David Jonq Wang, Palo Alto, CA (US)

(73) Assignee: BIOINTELLISENSE, INC., Redwood City, CA (US)

( * ) Notice: Subject to any disclaimer, the term of this patent is extended or adjusted under 35 U.S.C. 154(b) by 265 days.

(21) Appl. No.: 15/194,145

(22) Filed: Jun. 27, 2016

(65) Prior Publication Data
US 2017/0374036 A1    Dec. 28, 2017

(51) Int. Cl.
| | | |
|---|---|---|
| *H04L 29/06* | (2006.01) | |
| *G06N 5/02* | (2006.01) | |
| *A61B 5/00* | (2006.01) | |
| *A61B 5/02* | (2006.01) | |
| *A61B 5/0205* | (2006.01) | |
| *A61B 5/021* | (2006.01) | |
| *A61B 5/11* | (2006.01) | |
| *G06F 1/16* | (2006.01) | |

(52) U.S. Cl.
CPC ........ *H04L 63/0428* (2013.01); *A61B 5/0002* (2013.01); *A61B 5/02* (2013.01); *A61B 5/021* (2013.01); *A61B 5/0205* (2013.01); *A61B 5/1118* (2013.01); *G06F 1/163* (2013.01); *G06N 5/02* (2013.01)

(58) Field of Classification Search
CPC .......... G05B 1/01; H04L 63/105; G06F 1/163

USPC .......................................................... 713/168
See application file for complete search history.

(56) References Cited

U.S. PATENT DOCUMENTS

| | | | | |
|---|---|---|---|---|
| 8,209,564 | B2 * | 6/2012 | Vidal ........................ | G06F 8/65 714/38.1 |
| 2009/0021591 | A1 * | 1/2009 | Sako .................. | H04N 1/00339 348/211.2 |
| 2009/0237234 | A1 * | 9/2009 | McCaughan ............. | G01S 3/46 340/539.12 |
| 2013/0194066 | A1 * | 8/2013 | Rahman ................... | G05B 1/01 340/5.51 |
| 2015/0039880 | A1 * | 2/2015 | Aminzade ........... | H04L 41/0816 713/100 |
| 2016/0036826 | A1 * | 2/2016 | Pogorelik ............. | H04L 63/105 726/1 |

* cited by examiner

*Primary Examiner* — Bryan F Wright
(74) *Attorney, Agent, or Firm* — Maschoff Brennan

(57) ABSTRACT

A method to create autonomous decision logic (ADL) may include receiving a request to create the ADL. The request includes a selection of an input and a selection of an output. When executed by a client device, the ADL is configured to provide the output based at least partially on an identification of the input. The method further includes electronically packaging the input and the output to generate the ADL. The method includes sending the ADL via a transport layer to the client device for execution of the ADL on the client device. The client device is configured to generate encrypted data pertaining to the execution of the ADL. The method includes receiving, from the client device, the encrypted data pertaining to the execution of the ADL. The method further includes decrypting the encrypted data. The method includes presenting at least some of the decrypted data on a display.

20 Claims, 7 Drawing Sheets

METHODS AND SYSTEMS FOR JOURNALING AND COACHING USING A WEARABLE DEVICE

FIELD

The embodiments discussed in the present disclosure are related to wearable device journaling and coaching.

BACKGROUND

Some wearable devices have become a convenient way for users to track caloric consumption during the course of ordinary activities or exercise. Pedometers, for example, may be secured to the user's body and track the number of steps the user takes during the course of a day. Many wearable devices include a single accelerometer and simply display the number of steps to the user upon completion of an activity. Similarly, some mobile devices may come equipped with global position signal (GPS) receivers. The GPS receivers may interface with an application on the mobile device such that the user may track a distance covered while running or biking.

The subject matter claimed in the present disclosure is not limited to embodiments that solve any disadvantages or that operate only in environments such as those described above. Rather, this background is only provided to illustrate one example technology area where some embodiments described may be practiced. Furthermore, unless otherwise indicated, the materials described in the background section are not prior art to the claims in the present application and are not admitted to be prior art by inclusion in this section.

SUMMARY

According to an aspect of an embodiment, a method to create autonomous decision logic (ADL) may include receiving a request to create the ADL. The request includes a selection of an input and a selection of an output. When executed by a client device, the ADL is configured to provide the output based at least partially on an identification of the input. The method further includes electronically packaging the input and the output to generate the ADL. The method includes sending the ADL via a transport layer to the client device for execution of the ADL on the client device. The client device is configured to generate encrypted or obscured data pertaining to the execution of the ADL. The method includes receiving, from the client device, the encrypted or obscured data pertaining to the execution of the ADL. The method further includes decrypting the encrypted data or unobscuring the obscured data. The method includes presenting at least some of the decrypted data on a display.

The object and advantages of the implementations will be realized and achieved at least by the elements, features, and combinations particularly pointed out in the claims.

It is to be understood that both the foregoing general description and the following detailed description are given as examples and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

As wearable devices become increasingly ubiquitous, entities may desire to help wearers with various aspects of their lives. Some third party providers, might want to help encourage behavior. For example, a personal trainer may desire to continue to help a wearer achieve their fitness goals. Other companies may desire to encourage other types of behavior. Using the various techniques described herein, third party providers may create autonomous decision logic that may be send and executed on a tracked individual's device. The autonomous decision logic may process and collect various data which may be made available to the third party provider, who may in turn use that various data to further help the tracked individual.

With new technology, however, comes some degree of uncertainty. Some third party providers may be concerned about the security of autonomous decision logic they may send to a tracked individual. Using the various techniques described herein, third party providers may create secured autonomous decision logic, such as in a secure package, the contents of which may be obscured from all entities other than the third party provider who created the secured autonomous decision logic. The third party providers (including users/tracked individuals) may create and use autonomous decision logic for the purpose of journaling and coaching. User journaling may refer to tracking, storing and/or reporting various features of a tracked individual, including subjective opinions of the tracked individual. Coaching may refer to a message, suggestion or encouragement to motivate a tracked individual to do a particular activity. Taken together, coaching may ask a user for some input, whether subjective or objective, and request that the person journal the requested information. Coaching may also refer to the detection of one or more triggers that may cause a "coaching" event to appear on a user device. The triggers may include sensor information identified by the user device, time, or a coaching provider wishing to reach out to the user for any reason.

Figure 1:
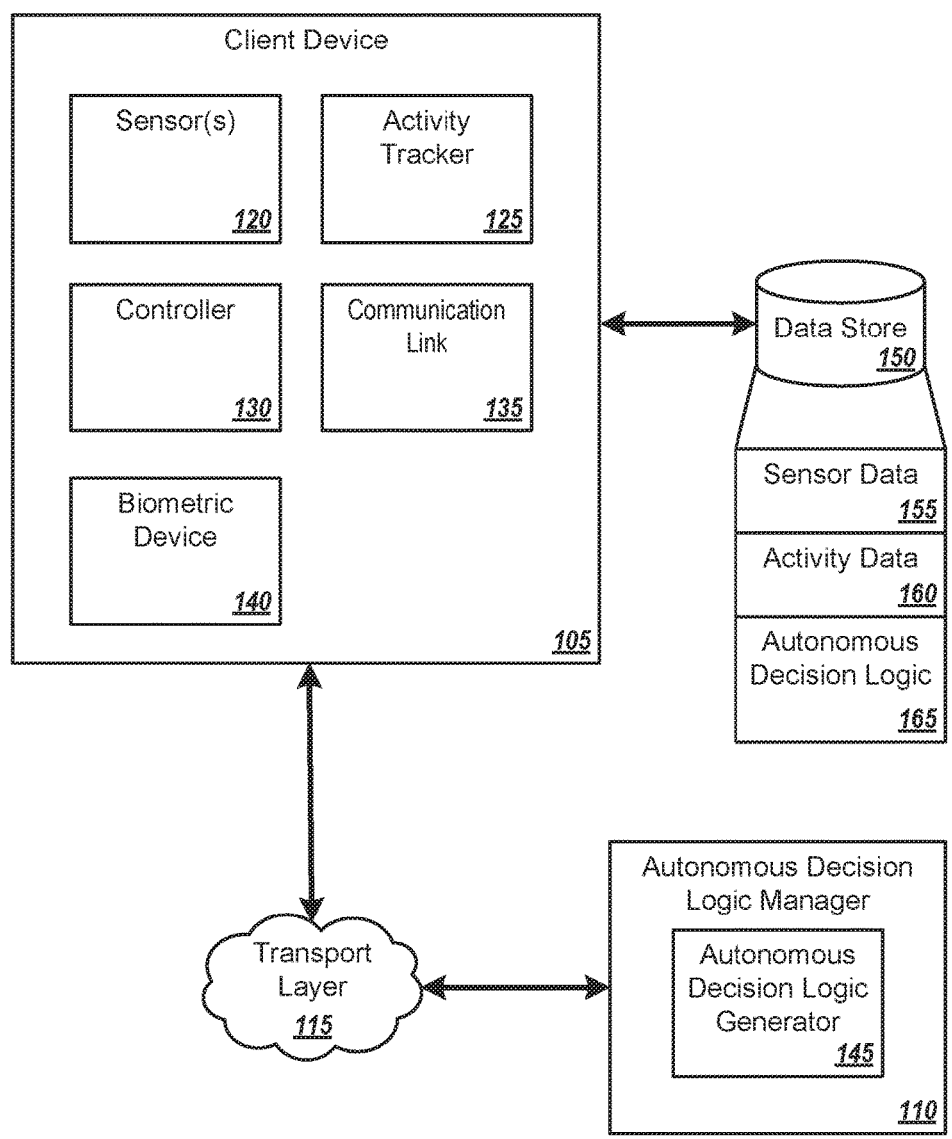
FIG. 1 is a block diagram of an example operating environment in which some embodiments may be implemented.

FIG. 1 is a block diagram of an example operating environment in which some embodiments may be implemented. The system 100 may include the client device 105, an autonomous decision logic manager 110, a transport layer 115, and a data store 150.

The client device 105 (herein referred to as "client device") may be a portable computing device, such as, and not limited to, an electronic wristwatch, arm band, chest strap, head band, bracelet, wristband, and the like. The client device 105 may run an operating system (OS) that manages hardware and software of the client device 105. The client device 105, the OS and modules within the OS can perform various operations, such as managing data associated with the client device 105 and a tracked individual who is associated with the client device 105. In at least one embodiment, the OS is a lightweight OS and may perform only the basic functions of a typical operating system. In at least one embodiment, the lightweight OS uses less than five kilobytes of RAM. In at least one embodiment, the client device 105 may execute applications and/or autonomous decision logic without an OS. In at least one embodiment, the client device 105 may include a task scheduler to manage execution of autonomous decision logic. The task scheduler may be any size, such as 128 bytes, 256 bytes, etc. In at least one embodiment, a task may be a few bytes. In some embodiments, the task scheduler may part of a lightweight OS. In some embodiments, the task scheduler may not be part of an OS.

The autonomous decision logic manager 110 may include one or more client or server computing devices, (such as a personal computer (PC), game console, set top box, laptop, mobile phone, smart phone, tablet computer, netbook computer, e-reader, personal digital assistant (PDA), or cellular phone, wearable device, rackmount server, a router computer, a server computer, a personal computer, a mainframe computer, a laptop computer, a web server, a proxy server, a desktop computer, etc.), data stores (e.g., hard disks, memories, databases), networks, software components, and/or hardware components. In some embodiments, the autonomous decision logic manager 110 may include a stand-alone application ("app") that may be downloadable either directly from a host or from an application store. The autonomous decision logic manager 110 may communicate with the client device 105 and/or the data store 150 via the transport layer 115. In at least one embodiment, the autonomous decision logic manager 110 provides autonomous decision logic to the client device 105. In at least one embodiment, the autonomous decision logic manager 110 receives data from the client device 105, creates or modifies autonomous decision logic based on the data from the client device 105 and sends the autonomous decision logic to the client device 105. In at least one embodiment, autonomous decision logic may be stored in the data store 150.

The transport layer 115 may include one or more wide area networks (WANs) and/or local area networks (LANs) that enable the client device 105 and the autonomous decision logic manager 110 to communicate with each other. For example, secured and/or encrypted data (e.g., autonomous decision logic data related to the execution of the autonomous decision logic) may be exchanged between the client device 105 and the autonomous decision logic manager 110. In some embodiments, the transport layer 115 includes the Internet, including a global internetwork formed by logical and physical connections between multiple WANs and/or LANs. Alternately or additionally, the transport layer 115 may include one or more cellular RF networks and/or one or more wired and/or wireless networks such as, but not limited to, 802.xx networks, Bluetooth access points, wireless access points, IP-based networks, meshed devices, or the like. The transport layer 115 may also include one or more servers that enable one type of network to interface with another type of network.

The client device 105 may include a sensor 120, an activity tracker 125, a controller 130, a communication link 135, and a biometric device 140. The controller 130 may include any type of controller, processor or logic. For example, the controller 130 may include some or all of the components of computing device 600 shown in FIG. 6. In some embodiments, one or more tracked individuals may include a person or user whose activity may be monitored by one or more of the sensor 120, activity tracker 125, communication link 135, and biometric device 140.

The sensor 120 may represent any hardware or software sensor capable to detect any characteristic of or near the client device 105 (such as data indicative of motion or environment), including but not limited to an accelerometer, gyroscope, altimeter, global positioning system (GPS), pedometer, magnetometer, a thermometer, a humidity sensor, a barometric pressure sensor, a GPS receiver, any other sensor that may detect motion, environmental, or human state, or any combination thereof. Any motion detected by the sensor 120 may be referred to as a motion characteristic. The sensor 120 may detect various motion patterns that may be associated with a particular movement of a tracked individual. The sensor 120 may include any suitable system, apparatus, device, or routine capable of detecting or determining one or more of the following: tilt, shake, rotation, swing, and any other motion. For example, the sensor 120 may detect that the client device 105 is periodically moving in a circular manner that is indicative of a tracked individual taking steps (e.g., walking, running). In some embodiments, the sensor 120 may be configured to detect or determine a location of a particular tracked individual. For example, the sensor 120 may include a GPS receiver, a Wi-Fi signal detector, a mobile phone communication network signal detector, a Bluetooth beacon detector, an Internet Protocol (IP) address detector or any other system, apparatus, device, or module that may detect or determine a location of the particular tracked individual. The location may include one or more labels or designations (e.g., home, work, gym). In some embodiments, the sensor 120 may be an integrated sensor that includes two or more different sensors integrated together. For example, the sensor 120 may be an integrated sensor that combines a three-dimensional (3D) accelerometer, a 3D gyroscope, and a 3D magnetometer. The sensor 120 may be wirelessly connected to the client device 105. In at least one embodiment, the sensor 120 is coupled to the client device 105 via a wired link. The client device 105 may include any number of sensors 120.

The activity tracker 125 may represent any hardware or software sensor or device that may be used to detect characteristics (or data indicative of the characteristics) of a tracked individual who is wearing the client device 105, including but not limited to, a heart rate monitor, a blood pressure monitor, thermometer, moisture sensor, respiration sensor, electrodermal activity sensor, sleep sensor, user interface (e.g., graphical user interface), etc. The activity tracker 125 may be used to identify characteristics of the tracked individual who is wearing the client device 105. In some embodiments, the heart rate monitor may be configured to measure or determine heart rate or indicators of heart rate. For example, the heart rate monitor may include one or more sensors (e.g., a photoresistor or a photodiode or the like) configured to detect a pulse, a skin temperature, etc. of a monitored tracked individual. The client device 105 may include any number of activity trackers 125.

In these or other embodiments, the activity tracker 125 may include a heart rate monitor may include one or more systems, apparatuses, devices, or modules configured to determine the heart rate based on the detected indicators. In some embodiments, an occurrence in a life of the particular tracked individual may include a heart rate of the particular tracked individual, a heart rate maintained by the particular tracked individual for a particular amount of time, a heart rate recovery time, etc., which may be determined by the controller 130 based on data received from one or more heart rate monitors or from other activity trackers or sensors.

In some embodiments, the activity tracker 125 may include a sleep sensor that is configured to determine whether a particular tracked individual is sleeping and/or to detect indicators that the particular tracked individual is sleeping. In some embodiments, the sleep sensor may include a physical sensor capable of detecting indicators of whether the particular tracked individual is sleeping, how much the particular tracked individual has slept, the sleep patterns of the particular tracked individual, how well the particular tracked individual has slept or a quality of the sleep of the particular tracked individual, etc. In these or other embodiments, the sleep sensor may include one or more systems, apparatuses, devices, or modules configured to determine that the particular tracked individual is sleeping based on the indicators.

The communication link 135 may provide any form of wired or wireless communication capability between the client device 105 and any other device. In some embodiments, the communication link 135 may include a radio frequency (RF) antenna. By way of example and not limitation, the communication link 135 may be configured to provide, via wireless mechanisms, LAN connectivity, Bluetooth connectivity, Wi-Fi connectivity, NFC connectivity, M2M connectivity, D2D connectivity, GSM connectivity, 3G connectivity, 4G connectivity, LTE connectivity, any other suitable communication capability, or any suitable combination thereof. The client device 105 may include any number of communication links 135.

The biometric device 140 may be configured to measure one or more unique biological or human characteristics of a monitored tracked individual. The measurements may include biometric measurements, such as fingerprints, iris, veins, DNA, etc. The biometric measurements may describe a unique feature of the tracked individual. For example, the biometric device 140 may include one or more of: a fingerprint scanner; a camera configured to capture an image of an iris; a device configured to measure the DNA of the tracked individual; a wearable electromyography sensor configured to capture electrical activity produced by the skeletal muscles of the tracked individual; or any other biometric device 140 configured to capture a biometric measurement associated with the tracked individual. The biometric device 140 may include a sensor or collection of sensors that may capture information (e.g., a human characteristic) suitable for determining an identity of the wearer (e.g., the tracked individual). Example human characteristics may include a sensor or set of sensors to detect fingerprints, iris, veins, DNA, chemicals in a blood stream, a hydration level of the wearer, skin and/or body temperature, a walking gait, etc. The client device 105 may include any number of biometric devices 140.

The data store 150 may be a persistent storage that is capable of storing data and may be part of the client device 105. A persistent storage unit may be a local storage unit or a remote storage unit. Persistent storage units may be a magnetic storage unit, optical storage unit, solid state storage unit, electronic storage units (main memory), or similar storage unit. Persistent storage units may be a monolithic device or a distributed set of devices. A 'set', as used herein, refers to any positive whole number of items. In one embodiment, the data store 150 may be internal to the client device 105. In another embodiment, the data store 150 may be external to the client device 105. As will be appreciated by those skilled in the art, in some implementations data store 150 may be a network-attached file server or a cloud-based file server, while in other implementations data store 150 might be some other type of persistent storage such as an object-oriented database, a relational database, and so forth. In at least one embodiment, the data store includes 256 kilobytes of flash memory. In some embodiments, the data store 150 includes 170 kilobytes of available flash memory. In some embodiments, the data store 150 includes 16 kilobytes of SRAM. In some embodiments, the data store 150 includes 8 kilobytes of SRAM.

The data store 150 may store data received from the sensor 120, the activity tracker 125, and/or the biometric device 140 such as, and not limited to, steps, calories, distance, time, current state of motion and/or the state of the tracked individual (e.g., stationary, walking, running), or any combination thereof (e.g., a sudden carry, which may be a change in motion relative to time), etc. Data obtained by the sensor 120 may be stored as sensor data 155. Data obtained by the activity tracker 125 may be stored as activity data 160.

The data store 150 may also store autonomous decision logic 165. The autonomous decision logic 165 may be received from any source, including from any client device, server machine, another data store, etc. For example, the data store 150 can receive autonomous decision logic created at the autonomous decision logic manager 110.

The autonomous decision logic manager 110 may include an autonomous decision logic generator 145 that may be configured to create autonomous decision logic. The autonomous decision logic generator 145 may include a template-based system that includes a set of predefined templates that a user may select from to create autonomous decision logic. The templates may include any number of building blocks (e.g., inputs, outputs) from basic building blocks to complex building blocks. The user may select (or define) various building blocks to create autonomous decision logic. Any logic including or behind the input and output may be obscured from one or more of the autonomous decision logic manager 110, transport layer 115, or the client device 105. In at least one embodiment, the autonomous decision logic may be secured (e.g., encrypted, obscured) in transport (e.g., before or while the autonomous decision logic is being sent to the client device 105). In at least one embodiment, the output of the autonomous decision logic may be obscured. In at least one embodiment, any input to the client device 105, which may be acted upon by autonomous decision logic may be obscured. In at least one embodiment, the autonomous decision logic manager 110 may include or perform any functionality or techniques described in U.S. patent application Ser. No. 15/007,727, filed on Jan. 27, 2016, the contents of which are incorporated by reference in their entirety.

In at least one embodiment, the autonomous decision logic may include a set of conditions that, when satisfied, may trigger an event (e.g., a change of state). The autonomous decision logic may identify and/or receive an input, determine whether the input satisfies a condition and, if so, the autonomous decision logic may identify a change in state. The input may include any type of data, such as time data, sensor data (e.g., sensor data 155), activity (e.g., activity data 160), biometric data, heart rate data, location data, and/or a modification of any input or calculation based on any input or combination of inputs (e.g., determining a workout intensity based on various factors such as time and heart rate). The change in state may include generating an output. Generating an output may include performing a data acquisition function, outputting a user message, and/or outputting a request for user input. For example, autonomous decision logic may include conditions and a trigger for when to present a particular message on a display device (e.g., a coaching event). The trigger may be activated by a single condition or by multiple conditions. In at least one embodiment, the trigger may be related to data received from one or more of the sensor 120, the activity tracker 125, or the biometric device. The event may include any action that may be performed in response to the trigger, including a change of state. For example, the event may include: displaying a message, requesting user input, recording information to a file, activating a haptic sensor (e.g., a vibration motor), providing a haptic response to a user (e.g., an electric shock), etc. In a specific example, the autonomous decision logic may identify a current time input (e.g., 8:00 am), which may satisfy a predetermined condition to output a message to a user requesting user data on the quality of the user's sleep.

In an example of a trigger with multiple conditions, one condition may be detection of a threshold amount of user movement and the second condition may be during a predetermined range of time (e.g., between 6:00-8:00 am on a weekday). The trigger may trigger an event to generate an output that may be displayed as a message on a display device once both the first and second conditions have been met. The message may be any message and, in some embodiments, may be a request for input from a tracked individual who is wearing the device. For example, the request may ask the tracked individual how well they slept and at least two options may be presented on the display. Any response received by the tracked individual (including a lack of response) may be stored according to rules specified in the autonomous decision logic and may be referred to as user journaling. In at least one embodiment, the output may include collecting data, such as raw data, from the sensor 120 and/or the activity tracker 125.

In at least one embodiment, the autonomous decision logic generator 145 may create autonomous decision logic based on parameters (e.g., conditions, triggers, and events) received from a system administrator, an end user, a tracked individual, or a combination thereof. In at least one embodiment, the autonomous decision logic generator 145 may create autonomous decision logic based on one or more inputs and/or outputs associated with other autonomous decision logic. For example, a first decision logic may receive a first set of inputs and may generate a first set of outputs. The autonomous decision logic generator 145 may create a second autonomous decision logic based on the first set of inputs, the first set of outputs, or a combination thereof. In at least one embodiment, the autonomous decision logic generator 145 may create additional autonomous decision logic based on the inputs and/or outputs of two or more other autonomous decision logic. The autonomous decision logic manager 110 may send autonomous decision logic to the client device 105 via the transport layer 115. In at least one embodiment, autonomous decision logic 165 are stored in the data store 150. In at least one embodiment, the autonomous decision logic generator 145 may secure the autonomous decision logic, such as by encrypting the autonomous decision logic, obscuring the autonomous decision logic, or by packaging the autonomous decision logic in a secure container. An example autonomous decision logic generator 145 is further described in conjunction with FIG. 3.

The controller 130 may be configured to receive and execute autonomous decision logic, including autonomous decision logic created by the autonomous decision logic generator 145 and/or autonomous decision logic 165 stored in the data store 150. When executing the autonomous decision logic, the controller 130 may use data stored in the data store 150 (e.g., sensor data 155, activity data 160) or may obtain direct, real-time readings from the sensor 120 and the activity tracker 125.

Example autonomous decision logic may relate to taking a survey from a tracked individual wearing the client device 105 to help rate that tracked individual's quality of sleep. For example, the controller 130 may detect the tracked individual has been sleeping for a predetermined number of hours (e.g., 2 hours). The controller 130 may detect sleep in any way, such as determining that the client device 105 has not moved for those 2 hours (based on readings from the sensor 120) and the current time (or start time) is during normal sleep hours (e.g., after midnight). In at least one embodiment, the sensor 120 may, additionally or alternatively, use the activity tracker 125 to detect that the tracked individual has achieved their resting heart rate and movements detected by the sensor 120 may be minimal to account for movements of the tracked individual while asleep. After detecting that the tracked individual has been sleeping for the predetermined number of hours, the controller 130 may detect that the tracked individual has begun movement indicative of someone who is awake. For example, the sensor 120 may collect data that the tracked individual has taken a threshold number of steps (e.g., 100). Once the controller 130 has determined that the tracked individual is awake, the controller 130 may output a survey to the tracked individual via a display on the client device 105. The survey may request, for example, a quality of sleep rating from the tracked individual. The controller 130 may store the quality of sleep rating in the data store 150. This example autonomous decision logic may be executed entirely on the client device 105. In at least one embodiment, the controller 130 may send the quality of sleep rating to the autonomous decision logic manager 110.

The controller 130 may perform various time measurements. For example, the controller may take a time snapshot at any point (e.g., when a condition is met, at a trigger, at an event/output). The controller 130 may also measure time between time snapshots. All time measurements may be stored in the data store 150. In at least one embodiment, 32-bit variables may be used to record the snapshots and/or measured time.

In at least one embodiment, autonomous decision logic 165 may be user-generated. For example, a personal trainer may desire to create personalized workouts and messages tailored to coach one or more people. The personal trainer may specify one or more conditions, triggers, and coaching events and may organize them within the autonomous decision logic. A personalized workout, for example, may include conditions for steps a tracked individual may take during a given amount of time. The tracked individual meeting a condition for doing a threshold amount of steps may trigger an event, which may include the client device outputting a personalized message of encouragement from the personal trainer to the tracked individual. In at least one embodiment, the personalized message may include a text, audio, and/or video message. As described, the autonomous decision logic may include any number of conditions, triggers and events. In at least one embodiment, the autonomous decision logic manager 110 may also provide a mechanism for users to share their user-generated autonomous decision logic and a mechanism for users to download user-generated autonomous decision logic that were created by other users. In at least one embodiment, users may subscribe to each other. Subscribing users may receive (e.g., push, pull, automatic) user-generated autonomous decision logic (which may be packaged as one or more software modules) created by those users to which they are subscribed. User-generation of autonomous decision logic 165 is further described in conjunction with FIG. 3.

In at least one embodiment, a tracked individual may browse previously created autonomous decision logic and/or programs related to previously created autonomous decision logic. For example, a user may desire to engage in weight loss activities. The user may browse other user-generated autonomous decision logic and may select one of the autonomous decision logic. The user may download the selected autonomous decision logic.

In at least one embodiment, the tracked individual may provide input to the client device 105 that the tracker user desires to achieve a goal. For example, the tracked individual may indicate that they desire to lose a certain number of pounds by a given date. The controller 130 may identify characteristics of the tracked individual and may identify autonomous decision logic suitable to help the tracked individual achieve the desired goal. For example, the controller 130 may identify height, weight, and age of the tracked individual and may place a request to the autonomous decision logic manager 110 to find individuals with a similar profile. The autonomous decision logic manager 110 may also identify autonomous decision logic that may have been used by a similar user with similar a height, weight, and age to achieve a similar goal. To identify such autonomous decision logic, the autonomous decision logic manager 110 may search a database based on one or more keywords, such as the information (e.g., height, weight, age) of the similar user. The controller 130 may automatically download and begin execution of such autonomous decision logic.

In at least one embodiment, the client device 105 may periodically monitor the autonomous decision logic and a goal of the tracked individual. For example, a first autonomous decision logic may help a tracked individual achieve part or some of a goal and a second autonomous decision logic may help the tracked individual finish achieving the goal. In response to detecting that the second autonomous decision logic may better help the tracked individual achieve their goal as compared to the first autonomous decision logic, the client device 105 may download or otherwise activate the second autonomous decision logic. For example, as a tracked individual gets more fit, a workout intensity of the user may need to increase to achieve a same heart rate.

In at least one embodiment, the controller 130 may create and/or manage one or more user profiles. The controller 130 may store data associated with the tracked individual in the data store 150. In at least one embodiment, the client device 105 is set to a default user profile to which all data is stored until one or more user profiles are set up.

In at least one embodiment, the client device 105 may periodically send data to the autonomous decision logic manager 110. In some embodiments, the client device 105 may send data to the autonomous decision logic manager 110 based on an elapsed time since the last batch of data was sent to the autonomous decision logic manager 110. In some embodiments, the client device 105 may send data to the autonomous decision logic manager 110 after regaining connectivity to the autonomous decision logic manager 110 after a loss of connectivity. The client device 105 may store and send raw data to the autonomous decision logic manager 110. In at least one embodiment, the client device 105 may process or pre-process the raw data to create intermediate data. The intermediate data may include high-pass filtered data, low-pass filtered data, or other extracted features (e.g., an output of a leaky bucket integrator).

In at least one embodiment, based on particular autonomous decision logic, the client device 105 may store raw data in response to one or more triggers, such as the first time someone walks during the day, or in response to detecting an anomalous heart rate reading. The autonomous decision logic may be used to track that raw data over time to determine patterns for the tracked individual.

In at least one embodiment, the client device 105 may use responses from the tracked individual to tailor device specific behaviors, such as validating that the tracked individual is doing something and/or for machine learning user behavior. For example, the client device 105 may use the sensor data 155 and/or the activity data 160 to determine that the tracked individual is running. Based on particular autonomous decision logic, the client device 105 may present a message to the tracked individual asking whether the tracked individual is running. If the client device 105 receives a "yes" answer from the tracked individual, the client device 105 may store the "yes" data in association with at least a portion of the sensor data 155 and/or the activity data 160 that was used to determine that the tracked individual was running. If the client device 105 receives a "no" answer from the tracked individual, the client device 105 may store the "no" data in association with at least a portion of the sensor data 155 and/or the activity data 160 that was used to determine that the tracked individual was running. In this manner, the client device 105 may determine which sensor data 155 and/or activity data 160 relates to the tracked individual running.

In at least one embodiment, the client device 105 may use autonomous decision logic to validate or authenticate an identity of the tracked individual, such as by using sensor data 155 and/or activity data 160 to analyze characteristics that may be unique to a tracked individual, such as a gait, a heart rate recovery, etc. For example, the controller 130 may develop a user profile for the tracked individual, such as by receiving a user profile or by developing the user profile over time. In at least one embodiment, the controller 130 may develop the user profile by determining that the tracked individual is performing an activity, and then presenting a challenge question to the tracked individual. Answers to the challenge question may be used to sort and categorize the data to develop the user profile. Over time, the controller 130 may determine a set of data that corresponds to a characteristic of the user, in this example, the gait of the tracked individual. The controller 130 may also collect raw data of the gait of the tracked individual, may send the raw data to the autonomous decision logic manager 110 where the server processes the raw data to determine a set of data that corresponds to the gait of the tracked individual. The controller 130 may periodically monitor the gait of the tracked individual to periodically validate that the tracked individual is wearing the client device 105. In at least one embodiment, a validation of the tracked individual may permit the tracked individual to perform various tasks, such as by connecting the communication link 135 (e.g., a NFC device) to provide payments when making a purchase. Should the controller 130 detect "gait" data that is inconsistent with the gait of the tracked individual, the controller 130 may request further authentication from the person who is wearing the client device 105 to determine whether they are the tracked individual. For example, the controller 130 may request that the person wearing the client device 105 authenticate themselves using the biometric device 140 or by answering a challenge question. In at least one embodiment, the client device 105 may be authenticated using techniques described in U.S. patent application Ser. No. 15/099,992, filed on Apr. 15, 2016, the contents of which are incorporated by reference in their entirety.

In some embodiments, the client device 105 may include speakers (not illustrated) that may play audio alerts (e.g., audio messages, music, audio calendar reminders, etc.). For example, the client device 105 may play as sound as part of an event associated with autonomous decision logic. In some embodiments, the client device 105 may include an audio sensor (e.g., a microphone) to receive audible input from the tracked individual.

In at least one embodiment, the client device 105 may send data or information collected or generated during execution of the autonomous decision logic to a second device of a user who created the autonomous decision logic (not illustrated). The client device 105 may secure such data or information. The second device may decrypt the data or information and/or further analyze the data or information. The second device may combine the data or information with other records, such as other records pertaining to the tracked individual. The second device may use the data or information to generate reports, graphs and/or determine rewards for the tracked individual.

Figure 2A:
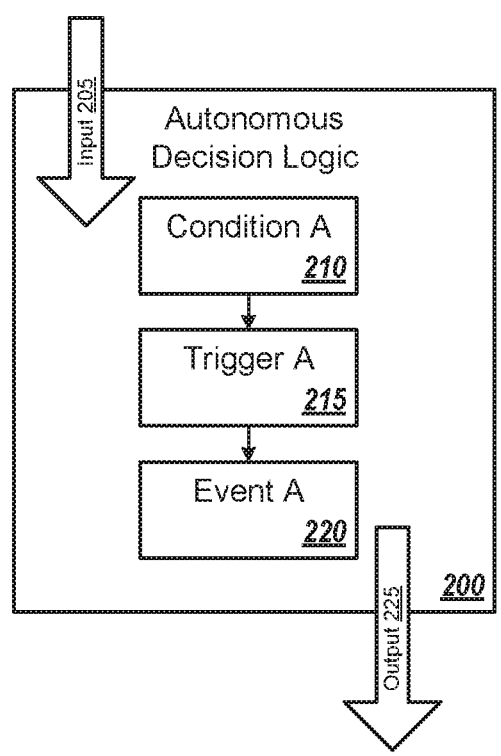
FIGS. 2A and 2B illustrate example autonomous decision logic in accordance with some embodiments.
Figure 2B:
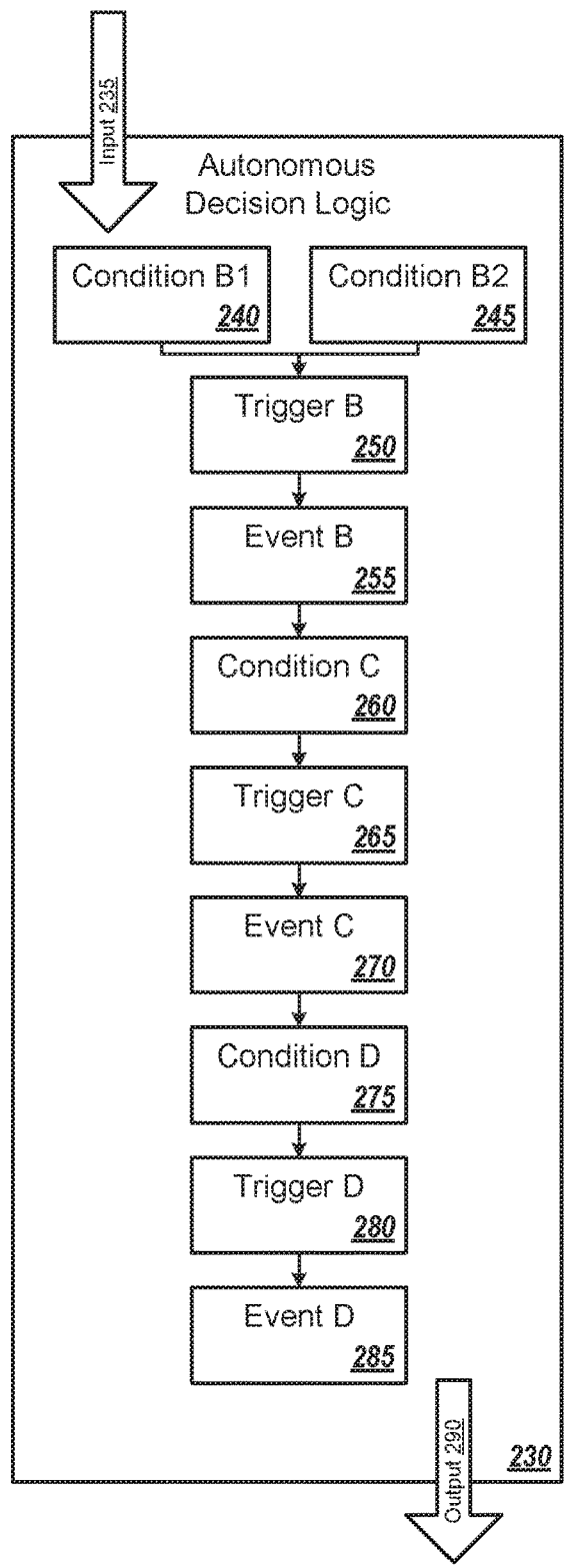

FIGS. 2A and 2B illustrate example autonomous decision logic 200 and 230 for a wearable device that may include decision logic in accordance with some embodiments. The autonomous decision logic may be portable and may be executed by a processor on top of or in addition to an operating system and/or firmware. In at least one embodiment, the autonomous decision logic is executable on a system that does not have an operating system. Autonomous decision logic may include an event variable that may be used to identify an event. The event variable may be any size. In at least one embodiment, the event variable is 1 byte, which may allow up to 256 individual events. In at least one embodiment, the event variable is 2 bytes, which may allow up to 65536 individual events. The autonomous decision logic 200 and 230 may include any number of inputs, conditions, triggers, events and outputs. Example inputs may include time (e.g., timer, alarm, countdown), physical indicators (e.g., steps, distance, calories, time), activity types (e.g., walking, running, stationary, sleeping, indeterminate activity), and user input (e.g., journaling input, answering a question, proving a rating, choosing from among a list of items, gesture-based input, such as a touch, tap, swirling motion, or a swipe, capacitive touch input, resistive touch input, discreet button-based input, tilt motion, audio input, voice input, video input). A time-based condition, for example, may be an alarm set to go off at a predetermined time. Alternatively, the time-based condition may be a countdown timer set to go off once the countdown is complete. In either case, the alarm going off may be the trigger 215. In at least one embodiment, the time-based condition may be set to "greater or equal to" an elapsed time. Example outputs may include setting a coaching event, a timer, logging information, causing a vibration of a client device, causing message to be presented on a display, causing a survey/journal to be presented, raw data collection, among others. In at least one embodiment, an output may include a determined state of the tracked individual, such as walking, running, stationary, sleeping, indeterminate activity. In at least one embodiment, an output may be used as an input to autonomous decision logic. In some embodiments, the time based condition may include saving sensor data or other data into memory.

In at least one embodiment the autonomous decision logic 200 and 230 may include one or more state machines. A state machine may be any device that stores a status of something (e.g., a tracked individual) at a given time and, based on one or more received inputs, may change the status and/or cause an event or output after any number of conditions are met. In some embodiments, the state machine may store an initial state, receive a set of possible inputs, determine, based on the received input(s) that a condition has been met, trigger an event based on the conditions having been met. The event may include changing to a new states that may result from the input and/or performing a set of possible actions or output events that result from the new state.

Turning now to FIG. 2A, in an example, the input 205 may include a tracked individual heart rate. The condition A 210 may include a maximum heart rate, which may be predetermined or specified by the tracked individual. The trigger A 215 may include a detection of the tracked individual heart rate being above the maximum heart rate, which triggers the event A. The event A may include generating an output 225, which may include a message (e.g., visual, audible, haptic) sent to the tracked individual via a display that their heart rate has exceeded the maximum heart rate.

FIG. 2B illustrates another example autonomous decision logic 230 with multiple conditions that may trigger a single event. The input 235 may include a time of day and a step counter. The condition B1 240 may include a condition for the time of day to be at the day start. The condition B2 245 may include a condition for a certain day (e.g., a weekday). When condition B1 240 is met, the time it is met may be recorded in a data store. When condition B2 245 is met, the day of the week may be recorded in a data store. Alternatively, when the condition B1 240 is met but B2 245 is not met, the day of the week (which, in this example, would be a weekend day) may also be recorded in a data store. When both the condition B1 240 and the condition B2 245 are met (e.g., it is the beginning of a weekday), then trigger B 250 may be used to trigger the event B 255 (e.g., start a timer for 4 hours). Condition C 260 may include a condition to check for tracked individual step until the timer has expired. When condition C 260 is met (e.g., the timer has not expired), trigger C 265 may trigger the event C 270 to generate an output, which may include loading a step counter or loading a record of steps from a data store.

Condition D 275 may include a minimum number of steps the tracked individual has taken. When the minimum number of steps is detected, condition D 275 and trigger D 280 initiates event D 285 to generate an output, which may include outputting the number of steps the tracked individual took, an amount of time it took the tracked individual to take the steps, the day of the week, the time of day, etc. In at least one embodiment, event D 285 may include presenting a message to the tracked individual via a display on a wearable client device. In at least one embodiment, any of the data collected from blocks 235-290 may be uploaded to a server.

Figure 3:
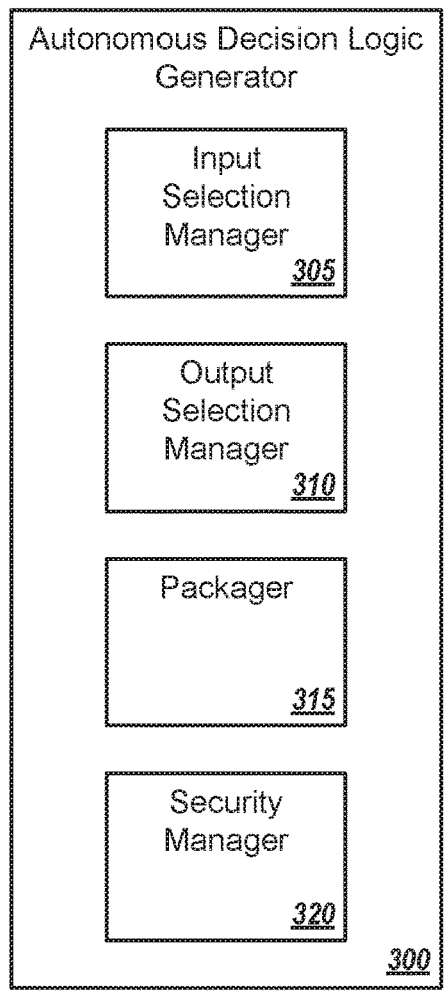
FIG. 3 illustrates an example autonomous decision logic generator.

An example of some data that may be recorded during execution of the autonomous decision logic 230 may include the following:

Transition to event A: idle,timerWait,dayStart
Transition to event B: timerWait,walkWait,timerExpire
Transition to event C: walkWait,idle,stepGoalMet
Output: idle,dayStart,loadTimer
Output: timerWait,timerExpire,loadStepCount
Output: walkWait,stepGoalMet,logEvent FIG. 3 illustrates an example autonomous decision logic generator 300. The autonomous decision logic generator 300 may be the same as or similar to the autonomous decision logic generator 145 of FIG. 1. Example autonomous decision logic created by the autonomous decision logic generator 300 may be the same as or similar to the autonomous decision logic 200 or 230, as further described in conjunction with FIGS. 2A and 2B, respectively. Further, the autonomous decision logic may be used for journaling and/or coaching, where journaling may include receiving and processing user input and where coaching may include encouraging the user to perform an action, which may be based at least in part on the user input.

In at least one embodiment, user-generated autonomous decision logic may be created using the autonomous decision logic generator 300. Any type of user may create autonomous decision logic using the autonomous decision logic generator 300, such as an individual, a personal trainer, a representative of a company, etc. The autonomous decision logic generator 300 may provide an interface for creating autonomous decision logic. The interface may be executed locally, web-based, or a combination thereof. For example, users may connect to a server which hosts the web-based interface. The web-based interface may be presented on a client device, such as via a browser. In some embodiments, the autonomous decision logic generator 300 may include a stand-alone application ("app") that may be downloaded. In at least one embodiment, the user may create the user-generated autonomous decision logic using the application (i.e., the autonomous decision logic generator 300), and then upload the user-generated autonomous decision logic to the autonomous decision logic manager 110 via the transport layer 115. The autonomous decision logic generator 300 may include an input selection manager 305, an output selection manager 310, a packager 315, and a security manager 320.

The input selection manager 305 permits a user to define what data the autonomous decision logic is to collect or receive as input. The selected input may include anything that may be received from a sensor (e.g., sensor 120 of FIG. 1), such a biometric input (e.g., retina, fingerprint), a touch on a capacitive or force sensor (e.g., touch, tap, touch and tap, swipe, press, press and hold). The input selection manager 305 may include a mechanism to receive a selection of one or more inputs from a user during the creation of an autonomous decision logic. The mechanism may include a graphical user interface (GUI) that may receive the input selection from the user. In at least one embodiment, the GUI may be an interface presented by a media viewer (e.g., an app, an application, a program, a software module/component, etc., that may be used to create autonomous decision logic). Some example GUIs include control elements in the form of a button (e.g., a button for selecting an input or output). However, it should be noted that various other control elements can be used for selection by a user such as a check box, a drop down menu, a text-input box, one or more radio buttons, a link, or any other user interface elements. In at least one embodiment, the input selection manager 305 may receive a selection of one or more inputs via an application program interface (API). The output selection manager 310 permits a user to define what the autonomous decision logic is to output. The output may include information to present on a display, a haptic (e.g., vibration) output, etc. The output may be a general output that may not elicit a response from a tracked individual. In at least one alternative embodiment, the output may be a request for information from the tracked individual, such as an answer to a challenge question, a text input, etc. The output selection manager 310 may include a mechanism to receive a selection of one or more outputs from a user during the creation of an autonomous decision logic. The mechanism may include a GUI that may receive the output selection from the user. The autonomous decision logic may also receive one or more conditions, triggers and/or events that may lead to an output, as further described in conjunction with FIGS. 2A and 2B.

In an example, a user may use the autonomous decision logic generator 300 to create autonomous decision logic directed to user journaling. User journaling may include tracking, storing and/or reporting various features of a tracked individual, including subjective opinions of the tracked individual. For example, a user journaling autonomous decision logic may be used to keep track of features such as a pain level, a mood, a quality of sleep, etc. User journaling autonomous decision logic may also be used for challenge questions to verify or authenticate an identity of the tracked individual.

In another example, a user may use the autonomous decision logic generator 300 to create autonomous decision logic directed to tracked individual coaching. The activity may include the tracked individual providing information, such as via a GUI. The activity may also be related to something outside of the client device 105. For example, a coaching autonomous decision logic may detect that a tracked individual is exercising and that the tracked individual is close to their personal best. The coaching autonomous decision logic may send a message (such as via a display of the client device) notifying the tracked individual that they are near their personal best. The message may include a coaching message that may include encouraging text to motivate the tracked individual to exceed their personal best. In at least one embodiment, the tracked individual may earn rewards for performing activities associated with a coaching autonomous decision logic. In at least one embodiment, coaching may include a communication means between a "cloud" object and the user's device. For example, the cloud object may include an external feature, such as weather data, and the coaching may suggest the user perform certain activities based on the external feature. In one example, the coaching may suggest a trail on which the user may jog when the weather is sunny outside and may suggest an indoor gym during inclement weather. Coaching may include detection of one or more triggers that may cause a coaching event to appear on the client device 105. The one or more triggers may include sensor information identified by the client device 105, time, or a coaching provider wishing to reach out to the user for any (or no) reason.

Subjective data of the tracked individual may be collected and stored along with other data that may be obtained via various sensors (e.g., sensor 120 of FIG. 1). The subjective opinions of the tracked individual to that may be obtained via various sensors may be analyzed in combination to better understand the tracked individual. For example, the tracked individual may indicate that they are in an irritable mood and a blood sugar sensor may detect low blood sugar during the times of the irritability of the tracked individual. In at least one embodiment, the autonomous decision logic may detect a correlation between sensor data and subjective data. The autonomous decision logic may also take action based on the correlation. As in the example above, the autonomous decision logic may detect a correlation between low blood sugar and irritability of the tracked individual. When the autonomous decision logic receives an input from the blood sugar sensor that the tracked individual's blood sugar is low, the autonomous decision logic may provide an output (such as a message) to the tracked individual to take action to remedy the low blood sugar.

The packager 315 may create the autonomous decision logic. To create the autonomous decision logic, the packager 315 may create a logical representation of the input(s), output(s), condition(s), trigger(s), and/or event(s). In at least one embodiment, the packager 315 may request and/or receive additional creation parameters for the autonomous decision logic, such as a name for the autonomous decision logic, a security setting, an expiration condition, a delivery option, etc. The security setting may include an encryption type or level, for example. The expiration condition may define a time or condition when the autonomous decision logic may stop working or when the autonomous decision logic may automatically delete itself from a device, etc. The delivery option may include a time-based delivery option, a fee-based delivery option, a particular transport method (or layer), etc. In at least one embodiment, the packager 315 may include a compiler.

The security manager 320 may apply security to the autonomous decision logic. In at least one embodiment, the autonomous decision logic is secured before it exits the autonomous decision logic generator 300. The autonomous decision logic generator 300 may secure the autonomous decision logic in any manner suitable for protecting the contents of the autonomous decision logic. For example, the autonomous decision logic generator 300 may encrypt the autonomous decision logic using one or more encryption keys. In at least one embodiment, the autonomous decision logic may be secured (e.g., encrypted, obscured) in transport (e.g., before or while the autonomous decision logic is being sent to a device (e.g., client device 105 of FIG. 1). The autonomous decision logic may be secured such that the inputs and/or outputs that were defined during the creation of the autonomous decision logic may not be easily accessible. In at least one embodiment, the autonomous decision logic generator 145 may secure the autonomous decision logic by abstracting some or all of the inputs and/or outputs of the autonomous decision logic. In at least one embodiment, output of the autonomous decision logic may be encrypted. In at least one embodiment, input to a device (e.g., client device 105 of FIG. 1), which may be acted upon by autonomous decision logic may be encrypted. Secured autonomous decision logic may be delivered to a client device (e.g., the client device 105 of FIG. 1) via a transport layer without the client device (e.g. the controller 130) or the transport layer being aware of the specific contents of the autonomous decision logic. Similarly, security may be defined for data that may be receives or generated by the autonomous decision logic. Such data may be encrypted before it is communicated to other device. The security manager 320 may ensure the autonomous decision logic includes instructions for securing such data.

In example of secured autonomous decision logic that is sent to a client device, during execution of the autonomous decision logic, a tracked individual may push a button on the client device. The client device only detects that the buttons was pressed. Without knowing the contents of the autonomous decision logic, the client device may not know why the button was pressed.

In at least one embodiment, the client device may at least partially decrypt encrypted autonomous decision logic to the extent that the client device may need to execute the autonomous decision logic. Any data or information obtained or generated during execution of the autonomous decision logic may be encrypted.

Figure 4:
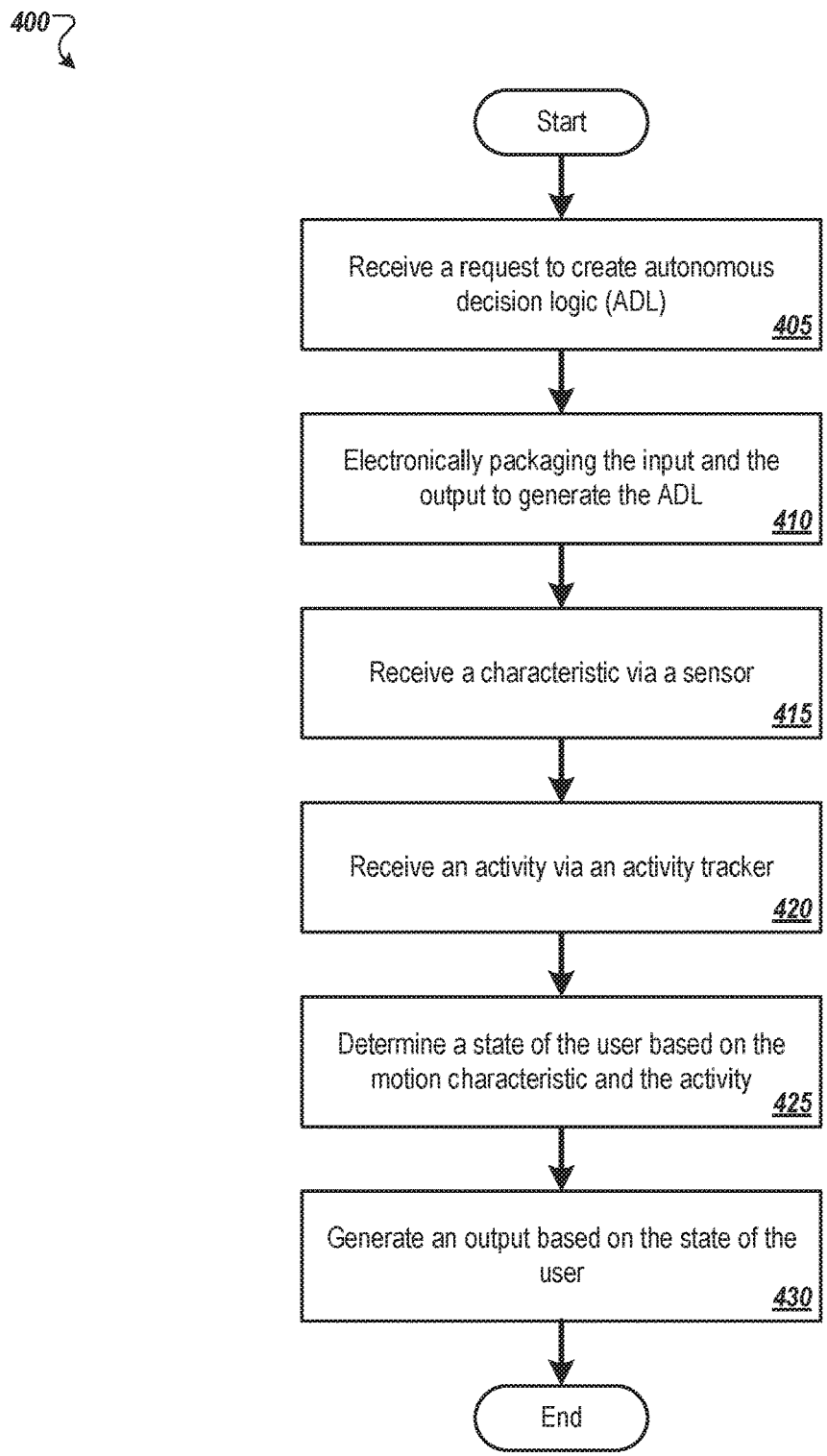
FIG. 4 illustrates a flow diagram of an example method that may be implemented in the operating environment of FIG. 1.

FIG. 4 illustrates a flow diagram of an example method 400 that may be implemented in the operating environment of FIG. 1, arranged in accordance with at least one embodiment described in the present disclosure. The method 400 may include a method of executing decision-based logic on a wearable device. The method may be performed by processing logic that may include hardware (circuitry, dedicated logic, etc.), software (such as is run on a general purpose computer system or a dedicated machine), or a combination of both, which processing logic may be included in the client device 105, controller 130 of FIG. 1 or another computer system or device. For simplicity of explanation, methods described herein are depicted and described as a series of acts. However, acts in accordance with this disclosure may occur in various orders and/or concurrently, and with other acts not presented and described herein. Further, not all illustrated acts may be required to implement the methods in accordance with the disclosed subject matter. In addition, those skilled in the art will understand and appreciate that the methods may alternatively be represented as a series of interrelated states via a state diagram or events. Additionally, the methods disclosed in this specification are capable of being stored on an article of manufacture, such as a non-transitory computer-readable medium, to facilitate transporting and transferring such methods to computing devices. The term article of manufacture, as used herein, is intended to encompass a computer program accessible from any computer-readable device or storage media. Although illustrated as discrete blocks, various blocks may be divided into additional blocks, combined into fewer blocks, or eliminated, depending on the desired implementation.

The method 400 may begin at block 405, where the processing logic may receive autonomous decision logic (e.g., portable, downloadable) via a transport layer. For example, the autonomous decision logic may be received from the autonomous decision logic manager 110 through the transport layer 115 using the communication link 135. The autonomous decision logic may be received, for example, when the wearable device is located in proximity to a wireless network location. At block 410, the processing logic may execute the autonomous decision logic. The received autonomous decision logic may be secured and/or encrypted. The processing logic may decrypt such autonomous decision logic. In at least one embodiment, executing the autonomous decision logic may include executing blocks 415, 420, 425 and 430. In at least one embodiment, the processing logic may continuously monitor for inputs. Alternatively, the processing logic may remain in a passive state until it receives an input. The input may include, for example, a motion characteristic and/or a fitness activity.

At block 415, the processing logic may receive a characteristic via a sensor. The characteristic may include, for example, directional movements received from an accelerometer sensor/device, among other characteristics, as further described in conjunction with FIG. 1. In this example, a motion characteristic may be indicative that a monitored individual is moving.

At block 420, the processing logic may receive an activity via an activity tracker. The activity may include, for example, a heart rate received from a heart rate sensor/device, among other activities, as further described in conjunction with FIG. 1. In this example, the activity may be indicative that a monitored individual is exercising strenuously.

At block 425, the processing logic may determine a state of the tracked individual based on the characteristic and the activity. For example, after receiving a first input (e.g., motion characteristic) that a tracked individual is moving at a relatively fast rate and a second input (e.g., fitness activity) that the heart rate of the tracked individual is in a cardio zone, the processing logic may determine that the tracked individual is in a "short-term exercising" state. In at least one embodiment, the processing logic may receive a further time-based input that the tracked individual has been in the exercising state for a predetermined amount of time. In response, the processing logic may determine that the tracked individual is in a "long-term exercising" state.

At block 430, the processing logic may generate an output based on the state of the tracked individual. The output may include a message for the tracked individual based on the state of the tracked individual. For example, the processing logic may determine an encouragement message for a tracked individual after detecting that the user has entered the short-term exercising state. The encouragement message may serve to encourage the tracked individual to continue to exercise so they may attain a "long-term exercising" state. In at least one embodiment, when generating the output based on the state of the tracked individual, the processing logic may send the message to the tracked individual, such as by displaying the message on a display, sending the message to the tracked individual via text, email, or SMS, among others. In at least one embodiment, when generating the output based on the state of the tracked individual, the processing logic may store the state of the tracked individual, the motion characteristic, and/or the fitness activity in a memory. In at least one embodiment, when generating the output based on the state of the tracked individual, the processing logic may collect and/or store additional data, such as from any of the sensors or activity monitors described herein. In at least one embodiment, when outputting the state of the tracked individual, the processing logic may send the state of the tracked individual, the characteristic, and/or the activity to a server via a network. In at least one embodiment, the processing logic may send raw sensor data, processed sensor data, and/or activity recognition data based on either raw or processed sensor data. For example, such data to be sent to the server may include raw acceleration data, high-pass filtered acceleration data, and steps derived from the high-pass filtered data. In at least one embodiment, the processing logic may detect a loss of a network connection of a wearable apparatus to a server, such as a server of the autonomous decision logic creator. The state of the tracked individual may be sent to the server in response to determining that the wearable apparatus has regained the network connection to the server. The processing logic may also send a multiple motion characteristics and multiple fitness activities to the server. In at least one embodiment, the processing logic may secure and/or encrypt any data or information it may send to a server.

Figure 5:
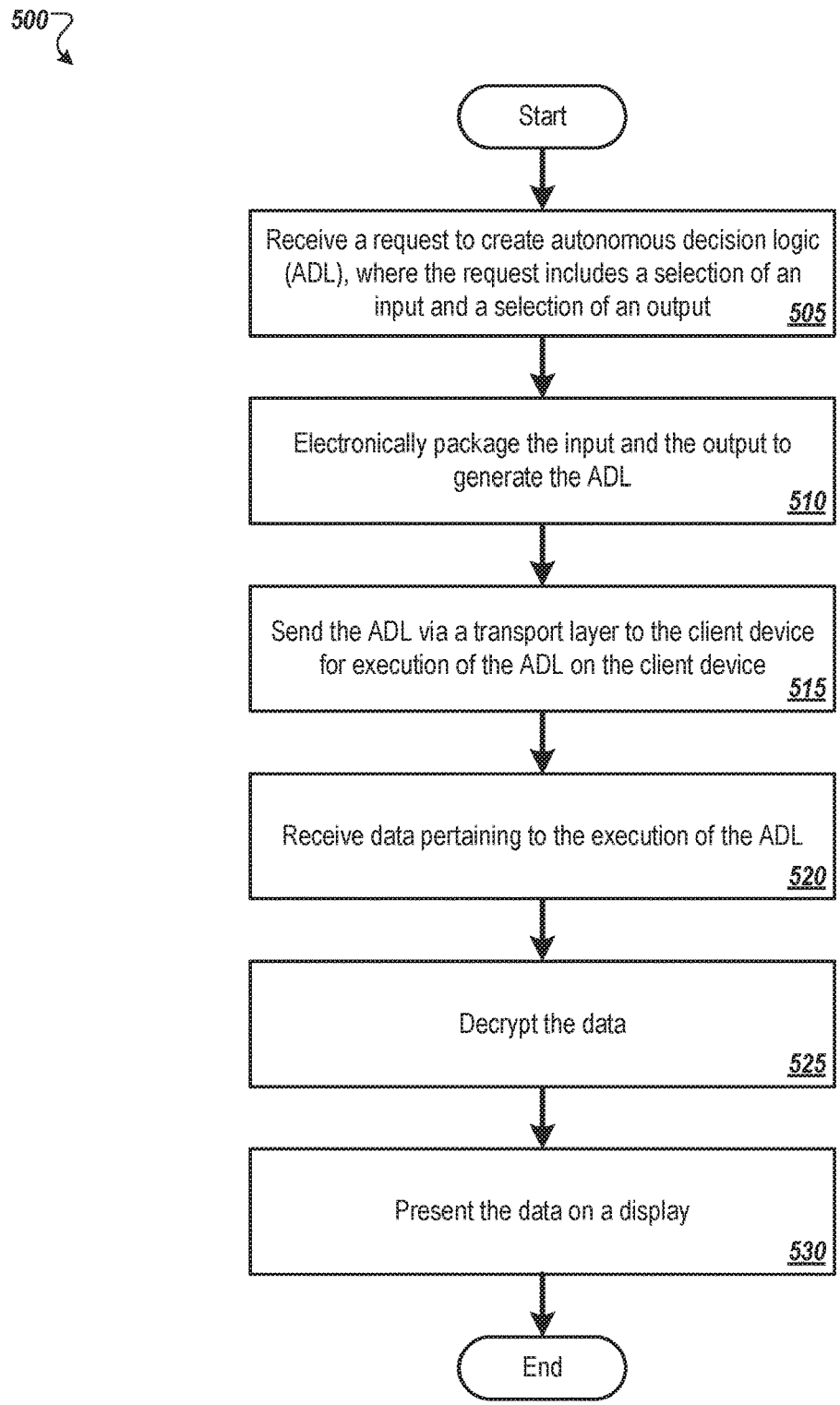
FIG. 5 illustrates a flow diagram of an example method to create autonomous decision logic implemented in the operating environment of FIG. 1, arranged in accordance with at least one embodiment described in the present disclosure.

FIG. 5 illustrates a flow diagram of an example method 500 to create autonomous decision logic implemented in the operating environment of FIG. 1, arranged in accordance with at least one embodiment described in the present disclosure. The method may be performed by processing logic that may include hardware (circuitry, dedicated logic, etc.), software (such as is run on a general purpose computer system or a dedicated machine), or a combination of both, which processing logic may be included in the autonomous decision generator 145 of FIG. 1 or another computer system or device.

At block 505, the processing logic may receive a request to create autonomous decision logic. The request may include a selection of an input and a selection of an output. The input may include at least one of: a characteristic of a device, a characteristic of a tracked individual, an activity of the tracked individual, or a characteristic of an environment. In at least one embodiment, the input includes a subjective opinion of the tracked individual. The processing logic may determine a correlation between at least two of the inputs. The output may include at least one of: a message displayed on a display device, a request for information from a tracked individual, or a haptic output. When executed by a client device, the autonomous decision logic is configured to provide the output based at least partially on an identification of the input. The encrypted data pertaining to the execution of the autonomous decision logic may include data received via the client device from the tracked individual. In at least one embodiment, the processing logic may receive an autonomous decision logic parameter that includes at least one of a security setting, an expiration condition, or a delivery option for the autonomous decision logic.

At block 510, the processing logic may electronically package the input and the output to generate the autonomous decision logic. The autonomous decision logic may be packaged in any format. In at least one embodiment, electronically packaging the input and the output to generate the autonomous decision logic may include encrypting the autonomous decision logic.

At block 515, the processing logic may send the autonomous decision logic via a transport layer to the client device for execution of the autonomous decision logic on the client device. The client device may be configured to generate encrypted data pertaining to the execution of the autonomous decision logic.

At block 520, the processing logic may receive, from the client device, the encrypted data pertaining to the execution of the autonomous decision logic. At block 525, the processing logic may decrypt the encrypted data. At block 530, the processing logic may present at least some of the decrypted data on a display.

Some embodiments may include a persistent and/or evolving autonomous decision logic within a wearable device. Some embodiments may be persistent, for example, by allowing the autonomous decision logic to continuously operate (e.g., assuming there is sufficient battery life). Some embodiments may be evolving, for example, by allowing the autonomous decision logic to update, for example, to perform new functions, store different data, move to different states, provide different notifications, and respond to different triggers, etc. based on any number of factors. An example includes updating any number of thresholds in response to user improvement. For example, as a tracked individual increases their fitness level, a minimum speed the user may run in order to achieve a desired heart rate may increase.

Figure 6:
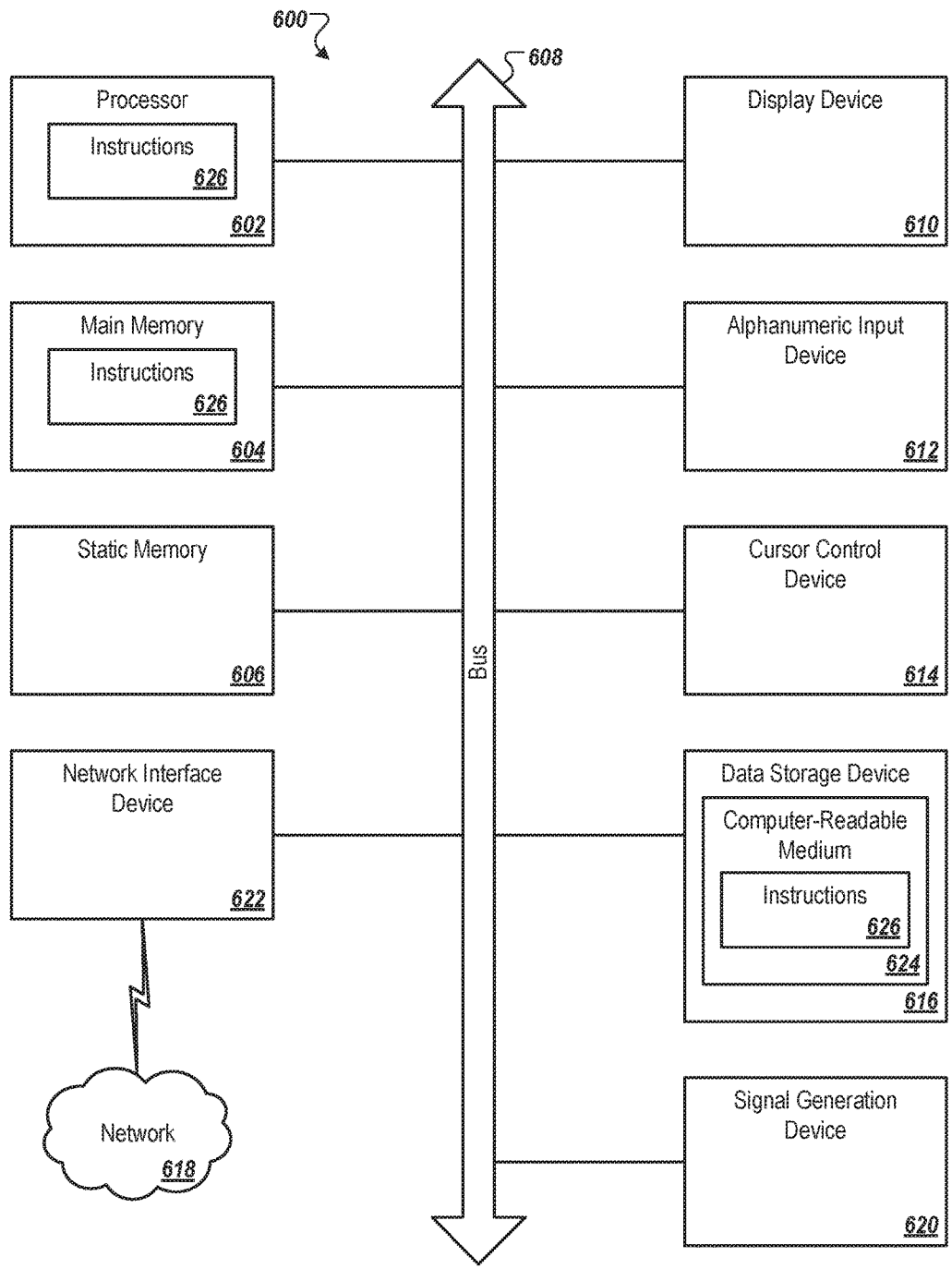
FIG. 6 shows an illustrative computing device for performing functionality to facilitate implementation of embodiments.

FIG. 6 illustrates a diagrammatic representation of a machine in the example form of a computing device 600 within which a set of instructions, for causing the machine to perform any one or more of the methodologies discussed herein, may be executed. The computing device 600 may include a mobile phone, a smart phone, a netbook computer, a rackmount server, a router computer, a server computer, a personal computer, a mainframe computer, a laptop computer, a tablet computer, a desktop computer etc., within which a set of instructions, for causing the machine to perform any one or more of the methodologies discussed herein, may be executed. In alternative embodiments, the machine may be connected (e.g., networked) to other machines in a LAN, an intranet, an extranet, or the Internet. The machine may operate in the capacity of a server machine in client-server network environment. The machine may be a personal computer (PC), a set-top box (STB), a server, a network router, switch or bridge, or any machine capable of executing a set of instructions (sequential or otherwise) that specify actions to be taken by that machine. Further, while only a single machine is illustrated, the term "machine" may also include any collection of machines that individually or jointly execute a set (or multiple sets) of instructions to perform any one or more of the methodologies discussed herein.

The example computing device 600 includes a processing device (e.g., a processor) 602, a main memory 604 (e.g., read-only memory (ROM), flash memory, dynamic random access memory (DRAM) such as synchronous DRAM (SDRAM)), a static memory 606 (e.g., static random access memory (SRAM)) and a data storage device 616, which communicate with each other via a bus 608.

Processing device 602 represents one or more general-purpose processing devices such as a microprocessor, central processing unit, or the like. More particularly, the processing device 602 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 602 may also be one or more special-purpose processing devices such as an application specific integrated circuit (ASIC), a field programmable gate array (FPGA), a digital signal processor (DSP), network processor, or the like. The processing device 602 is configured to execute instructions 626 for performing the operations and steps discussed herein.

The computing device 600 may further include a network interface device 622 which may communicate with a network 618. The computing device 600 also may include a display device 610 (e.g., a liquid crystal display (LCD) or an organic light emitting diode (OLED)), an alphanumeric input device 612 (e.g., a keyboard), a cursor control device 614 (e.g., a mouse) and a signal generation device 620 (e.g., a speaker). In one implementation, the display device 610, the alphanumeric input device 612, and the cursor control device 614 may be combined into a single component or device (e.g., an LCD touch screen).

The data storage device 616 may include a computer-readable storage medium 624 on which is stored one or more sets of instructions 626 embodying any one or more of the methodologies or functions described herein. The instructions 626 may also reside, completely or at least partially, within the main memory 604 and/or within the processing device 602 during execution thereof by the computing device 600, the main memory 604 and the processing device 602 also constituting computer-readable media. The instructions may further be transmitted or received over a network 618 via the network interface device 622.

While the computer-readable storage medium 626 is shown in an example embodiment to be a single medium, the term "computer-readable storage medium" may include a single medium or multiple media (e.g., a centralized or distributed database and/or associated caches and servers) that store the one or more sets of instructions. The term "computer-readable storage medium" may also include any medium that is capable of storing, encoding or carrying a set of instructions for execution by the machine and that cause the machine to perform any one or more of the methodologies of the present disclosure. The term "computer-readable storage medium" may accordingly be taken to include, but not be limited to, solid-state memories, optical media and magnetic media.

In these or other embodiments, image files associated with images may include metadata such as geolocation data, audio data, voice tag data, motion data, biological data, temperature data, a time stamp, a date stamp, user tag data, barometric pressure data, people data, and/or camera orientation data. Some or all of the metadata of the image files may be used as annotations for the corresponding image.

Terms used herein and especially in the appended claims (e.g., bodies of the appended claims) are generally intended as "open" terms (e.g., the term "including" may be interpreted as "including, but not limited to," the term "having" may be interpreted as "having at least," the term "includes" may be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases may not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" may be interpreted to mean "at least one" or "one or more"); the same holds true for the use of definite articles used to introduce claim recitations.

In addition, even if a specific number of an introduced claim recitation is explicitly recited, those skilled in the art will recognize that such recitation may be interpreted to mean at least the recited number (e.g., the bare recitation of "two recitations," without other modifiers, means at least two recitations, or two or more recitations). Further, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, may be understood to contemplate the possibilities of including one of the terms, either of the terms, or both terms. For example, the phrase "A or B" may be understood to include the possibilities of "A" or "B" or "A and B."

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general purpose or special purpose computer. Combinations of the above may also be included within the scope of computer-readable media.

Computer-executable instructions may include, for example, instructions and data which cause a general purpose computer, special purpose computer, or special purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general purpose hardware (e.g., computer-readable media, processing devices, etc.) of the computing system. In some embodiments, the different components, modules, engines, and services described herein may be implemented as objects or processes that execute on the computing system (e.g., as separate threads). While some of the system and methods described herein are generally described as being implemented in software (stored on and/or executed by general purpose hardware), specific hardware implementations or a combination of software and specific hardware implementations are also possible and contemplated. In this description, a "computing entity" may be any computing system as previously defined herein, or any module or combination of modulates running on a computing system.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it may be understood that the various changes, substitutions, and alterations may be made hereto without departing from the spirit and scope of the present disclosure.

The term "substantially" means within 5% or 10% of the value referred to or within manufacturing tolerances.

Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

What is claimed is:

1. A method comprising:
   receiving a request to create autonomous decision logic (ADL), wherein the request includes a selection of an input, a selection of an output, a selection of a security setting that includes encryption information for data generated by the ADL; and an expiration condition for the ADL, where the expiration condition is a predetermined time or condition, and wherein when executed by a client device, the ADL is configured to provide the output based at least partially on an identification of the input;

electronically packaging the input, the output, and the security setting to generate the ADL;

sending the ADL via a transport layer to the client device for execution of the ADL on the client device, wherein the client device is configured to generate encrypted data pertaining to the execution of the ADL and based on the security setting;

receiving, from the client device, the encrypted data pertaining to the execution of the ADL;

decrypting the encrypted data;

presenting at least some of the decrypted data on a display; and stopping execution of the ADL or deleting the ADL from the client device based on a satisfaction of the expiration condition.

2. The method of claim 1, wherein electronically packaging the input and the output to generate the ADL comprises encrypting the ADL.

3. The method of claim 1, wherein the input includes at least one of: a characteristic of a device, a characteristic of a tracked individual, an activity of the tracked individual, or a characteristic of an environment.

4. The method of claim 3, wherein the input includes a subjective opinion of the tracked individual, the method further comprising determining a correlation between at least two of the inputs.

5. The method of claim 3, wherein the encrypted data pertaining to the execution of the ADL comprises data received via the client device from the tracked individual.

6. The method of claim 1, wherein the output includes at least one of: a message displayed on a display device, a request for information from a tracked individual, or a haptic output.

7. The method of claim 1 further comprising receiving an ADL parameter that includes a delivery option for the ADL.

8. A system comprising:

a memory; and a processor operatively coupled to the memory, the processor being configured to:

receive a request to create autonomous decision logic (ADL), wherein the request includes a selection of an input, a selection of an output, a selection of a security setting that includes encryption information for data generated by the ADL; and an expiration condition for the ADL, where the expiration condition is a pre-determined time or condition, and wherein when executed by a client device, the ADL is configured to provide the output based at least partially on an identification of the input;

electronically package the input, the output, and the security setting to generate the ADL;

send the ADL via a transport layer to the client device for execution of the ADL on the client device, wherein the client device is configured to generate encrypted data pertaining to the execution of the ADL and based on the security setting;

receive, from the client device, the encrypted data pertaining to the execution of the ADL;

decrypt the encrypted data;

present at least some of the decrypted data on a display; and stop execution of the ADL or delete the ADL from the client device based on a satisfaction of the expiration condition.

9. The system of claim 8, wherein when electronically packaging the input and the output to generate the ADL, the processor is configured to encrypt the ADL.

10. The system of claim 8, wherein the input includes at least one of: a characteristic of a device, a characteristic of a tracked individual, an activity of the tracked individual, or a characteristic of an environment.

11. The system of claim 10, wherein the input includes a subjective opinion of the tracked individual, the processor further being configured to determine a correlation between at least two of the inputs.

12. The system of claim 10, wherein the encrypted data pertaining to the execution of the ADL comprises data received via the client device from the tracked individual.

13. The system of claim 8, wherein the output includes at least one of: a message displayed on a display device, a request for information from a tracked individual, or a haptic output.

14. The system of claim 8, wherein the processor is further configured to receive an ADL parameter that includes a delivery option for the ADL.

15. A non-transitory computer readable storage medium comprising instructions that, when executed by a processor, cause a system to perform operations comprising:

receive a request to create autonomous decision logic (ADL), wherein the request includes a selection of an input, a selection of an output, a selection of a security setting that includes encryption information for data generated by the ADL; and an expiration condition for the ADL, where the expiration condition is a pre-determined time or condition, and wherein when executed by a client device, the ADL is configured to provide the output based at least partially on an identification of the input;

electronically package the input, the output, and the security setting to generate the ADL;

send the ADL via a transport layer to the client device for execution of the ADL on the client device, wherein the client device is configured to generate encrypted data pertaining to the execution of the ADL and based on the security setting;

receive, from the client device, the encrypted data pertaining to the execution of the ADL;

decrypt the encrypted data;

present at least some of the decrypted data on a display; and stop execution of the ADL or delete the ADL from the client device based on a satisfaction of the expiration condition.

16. The non-transitory computer readable storage medium of claim 15, wherein electronically packaging the input and the output to generate the ADL comprises encrypting the ADL.

17. The non-transitory computer readable storage medium of claim 15, wherein the input includes at least one of: a characteristic of a device, a characteristic of a tracked individual, an activity of the tracked individual, or a characteristic of an environment.

18. The non-transitory computer readable storage medium of claim 17, wherein the input includes a subjective opinion of the tracked individual, the operations further comprising determining a correlation between at least two of the inputs.

19. The non-transitory computer readable storage medium of claim 17, wherein the encrypted data pertaining to the execution of the ADL comprises data received via the client device from the tracked individual.

20. The non-transitory computer readable storage medium of claim 15, wherein the output includes at least one of: a message displayed on a display device, a request for information from a tracked individual, or a haptic output.

* * * * *